United States Patent [19]
Gaster

[11] Patent Number: 5,972,979
[45] Date of Patent: Oct. 26, 1999

[54] TRICYCLIC SPIRO COMPOUNDS AS 5HT$_{1D}$ RECEPTOR ANTAGONISTS

[75] Inventor: Laramie Mary Gaster, Bishops Stortford, United Kingdom

[73] Assignee: SmithKline Beecham p.l.c., Brentford, United Kingdom

[21] Appl. No.: 09/077,263

[22] PCT Filed: Nov. 15, 1996

[86] PCT No.: PCT/EP96/05045

§ 371 Date: Mar. 10, 1999

§ 102(e) Date: Mar. 10, 1999

[87] PCT Pub. No.: WO97/19070

PCT Pub. Date: May 29, 1997

[30] Foreign Application Priority Data

Nov. 22, 1995 [GB] United Kingdom .................. 9523894
Mar. 29, 1996 [GB] United Kingdom .................. 9606649
Apr. 4, 1996 [GB] United Kingdom .................. 9607179

[51] Int. Cl.⁶ ........................ C07D 491/107; A61K 31/41
[52] U.S. Cl. ................................ 514/364; 548/131
[58] Field of Search ............................. 548/131; 514/364

[56] References Cited

FOREIGN PATENT DOCUMENTS

| WO 95/32967 | 12/1995 | WIPO . |
| WO 96/04269 | 2/1996 | WIPO . |
| WO 96/06079 | 2/1996 | WIPO . |
| 96/11934 | 4/1996 | WIPO .................................. 548/131 |
| WO 96/19477 | 6/1996 | WIPO . |
| WO 96/23785 | 8/1996 | WIPO . |
| WO 96/31508 | 10/1996 | WIPO . |

OTHER PUBLICATIONS

Clitherow, et al., J. of Med. Chem., 1994, vol. 37, No. 15, pp. 2253–2257.

*Primary Examiner*—Robert Gerstl
*Attorney, Agent, or Firm*—Wayne J Dustman; William T. King; Charles M. Kinzig

[57] ABSTRACT

Novel heterocyclic derivatives, processes for their preparation, pharmaceutical compositions containing them and their use as medicaments are disclosed.

8 Claims, No Drawings

TRICYCLIC SPIRO COMPOUNDS AS 5HT$_{1D}$ RECEPTOR ANTAGONISTS

The present invention relates to novel heterocyclic derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are said to be of use in the treatment of various CNS disorders. The 5HT$_{1D\beta}$ receptor has now been reclassified as the 5HT$_{1B}$ receptor (P. R Hartig et al Trends in Pharmacological Science, 1996, 17, 103–105.

A structurally distinct class of compounds have now been discovered and have been found to exhibit 5HT$_{1B}$ antagonist activity. In a first aspect, the present invention therefore provides a compound of formula (I) or a salt or N-oxide thereof:

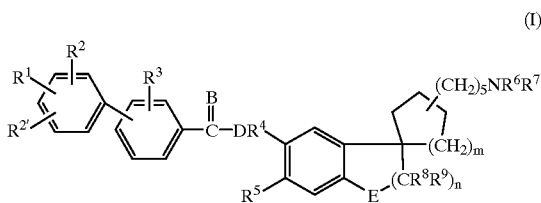

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^{10}$, SOR$^{10}$, SO$_2$R$^{10}$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 and R$^{13}$ is hydrogen, C$_{1-6}$alkyl or optionally substituted aryl; or R$^1$ is a group —X—R where X is a bond, O, S, CH$_2$, C=O, NHCO, NAlkylCO, NH or NAlkyl where Alkyl is C$_{1-6}$alkyl and R is an optionally substituted bicyclic heterocyclic ring or monocyclic 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ areas defined for R$^1$;

B is oxygen or sulphur;

D is nitrogen, carbon or a CH group;

R$^4$ is hydrogen or C$_{1-6}$alkyl;

R$^5$ is hydrogen or C$_{1-6}$alkyl or R$^4$ and R$^5$ together form a group —A— where A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$;

R$^6$ and R$^7$ are independently hydrogen, C$_{1-6}$alkyl or R$^6$ and R$^7$ are joined to form an optionally substituted 5- to 7-membered heterocyclic ring optionally containing a further heteroatom selected from oxygen, nitrogen or sulphur;

R$^8$ and R$^9$ are independently hydrogen or C$_{1-6}$alkyl;

E is oxygen, CR$^{15}$R$^{16}$ or NR$^{17}$ where R$^{15}$, R$^{16}$ and R$^{17}$ are independently hydrogen or C$_{1-6}$alkyl or E is a group S(O)$_b$ where b is 1, 2 or 3;

m is 1, 2 or 3;

n is 1, 2 or 3; and s is 0, 1, 2, 3 or 4.

C$_{1-6}$alkyl groups, whether alone or as part of another group, may be straight chain or branched. As used herein the term aryl means phenyl and naphthyl groups.

Suitably R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$akoxy, C$_{1-6}$alkoxyC$_{1-6}$alkoxy, acyl, nitro, trifluoromethyl, cyano, SR$^{10}$, SOR$^{10}$, SO$_2$R$^{10}$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^9$, R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 and R$^{13}$ is hydrogen, C$_{1-6}$alkyl or optionally substituted aryl. Preferred groups include NR$^{12}$COR$^{13}$.

Suitably R$^1$ is a group —X—R where X is a bond, O, S, CH$_2$, C=O, NHCO, NAlkylCO, NH or NAlkyl where Alkyl is C$_{1-6}$alkyl and R is an optionally substituted bicyclic heterocyclic ring or monocyclic 5 to 7-membered heterocyclic ring said bicyclic or monocyclic rings containing 1 to 4 heteroatoms selected from oxygen, nitrogen or sulphur. Preferably X is a bond. Preferably R is a 5 to 7-membered heterocyclic ring. Suitable groups R include aromatic groups such as thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. Saturated and partially saturated rings are also within the scope of the invention, in particular rings including an oxo or thioxo moiety such as lactams and thiolactams. The heterocyclic rings can be linked to the remainder of the molecule via a carbon atom or, when present, a nitrogen atom. Suitable substituents for these rings include R$^2$ and R$^3$ groups as defined above. Preferably R is optionally substituted oxadiazolyl or an optionally substituted lactam ring. Preferred substituents for oxadiazolyl groups include C$_{1-6}$alkyl such as methyl. Most preferably R is a 5-methyl-1,2,4-oxadiazol-3-yl group.

Suitably R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alky, acyl, aryl, acyloxy, hydroxy, nitro, trifluoromethyl, cyano, CO$_2$R$^{10}$, CONR$^{10}$R$^{11}$, NR$^{10}$R$^{11}$ where R$^9$, R$^{10}$ and R$^{11}$ are independently hydrogen or C$_{1-6}$alkyl. Preferably R$^2$ is C$_{1-6}$alkyl, in particular methyl. Preferably R$^3$ is hydrogen.

Suitably R$^4$ is hydrogen or C$_{1-6}$alkyl and R$^5$ is hydrogen or C$_{1-6}$alkyl or R$^4$ and R$^5$ together form a group —A— where A is (CR$^{13}$R$^{14}$)$_q$ where q is 2, 3 or 4 and R$^{13}$ and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$. Preferably R$^4$ and R$^5$ form a group —A—. Preferably A is (CH$_2$)$_2$.

Suitably R$^6$ and R$^7$ are indepandantly hydrogen, C$_{1-6}$alkyl or R$^6$ and R$^7$ are joined to form an optionally substituted 5- to 7-membered heterocyclic ring optionally containing a further heteroatom selected from oxygen, nitrogen or sulphur. Example sof such rings include morpholine and piperidine rings. Optional substituents include $C_{1-6}$alkyl. Preferably $R^6$ and $R^7$ are both $C_{1-6}$alkyl, in particular methyl.

Suitably $R^8$ and $R^9$ are independently hydrogen or $C_{1-6}$alkyl, preferably $R^8$ and $R^9$ are both hydrogen.

Suitably m is 1, 2 or 3. Preferably m is 2 forming a cyclohexane ring.

Suitably E is oxygen, $CR^{15}R^{16}$ or $NR^{17}$ where $R^{15}$, $R^{16}$ and $R^{17}$ are independently hydrogen or $C_{1-6}$alkyl or E is a group $S(O)_b$ where b is 1, 2 or 3. Preferably E is oxygen or sulphur, most preferably E is oxygen.

Suitably n is 1, 2 or 3, preferably n is 1.

Suitably s is 0, 1, 2, 3 or 4, preferably s is 0.

Particularly preferred compounds of the invention include:

2,3-Dihydro-4'-dimethylamino-5-[2'-methyl-4'-(5-methyl-1,2,4-oxadiazol-3-yl)biphenyl-4-carbonylamino]spiro[benzofuran-3,1'-cyclohexane], 4'-Dimethylamino-5-[2'-methyl-4'-(5-methyl-1,2,4-oxadiazol-3-yl)biphenyl-4-carbonyl]-2,3,6,7-tetrahydrospiro[furo[2,3-f]indole-3,1'-cyclohexane], or pharmaceutically acceptable salts thereof.

Preferred salts of the compounds of formula (I) are pharmaceutically acceptable salts. These include acid addition salts such as hydrochlorides, hydrobromides, phosphates acetates. fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) for compounds where D is nitrogen and B is oxygen reaction of a compound of formula (II):

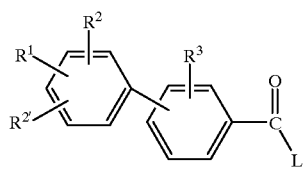

(II)

in which $R^1$, $R^2$, $R^{2'}$ and $R^3$ are as defined in formula (I) and L is a leaving group, with a compound of formula (III):

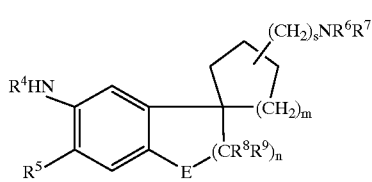

(III)

wherein $R^4$, $R^5$, $R^6$, $R^7$, $R^8$, $R^9$, E, m, n and s are as defined in formula (I) and optionally thereafter in any order:

converting a compound of formula (I) into another compound of formula (I)

forming a pharmaceutically acceptable salt or N-oxide thereof.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazide. Preferably the group L is halo, particularly chloro.

A compound of formulae (II) and (III) are typically reacted together in an inert organic solvent such as DMF, THF or dichloromethane at ambient or elevated temperature in the presence of a base such as an alkali metal hydroxide, triethylamine or pyridine.

Alternatively L is an ester forming group such that the resulting esters of formula (II) can be reacted with compounds of formula (III) in the presence of an organoaluminium reagent such as trimethylaluminium. Such a reaction is typically carried out in the presence of an inert solvent such as toluene.

Intermediate compounds of formulae (II) can be prepared using standard procedures such as those outlined in EPA 533266/7/8. Intermediate compounds of formula (III) can be prepared using standard procedures. Certain intermediate compounds of formula (III) are novel and form a further aspect of the invention.

An alternative process which can be used to prepare compounds of the invention involves a reductive amination end-step as exemplified herein.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Compounds of formula (I) can be converted into further compounds of formula (I) using standard procedures known in the art. For example amino groups can be alkylated using a suitable base and an alkyl halide.

Salts and N-oxides can be prepared using standard procedures. For example N-oxides can be prepared using meta-chloroperoxybenzoic acid or hydrogen peroxide.

$5HT_{1B}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders. $5HT_{1B}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

Dimethyl 4-cyano-4-(2-fluorophenyl)heptanedioate

2-Fluorophenylacetonitrile (39.85 g, 0.29 mol) and ethyl acrylate (96 ml, 0.89 mol) were stirred at reflux in t-butanol (400 ml) as benzyltrimethylammonium hydroxide (40% solution in MeOH, 140 ml, 0.30 mol) was added portionwise over 48 h. The mixture was then evaporated to dryness, dissolved in ethyl acetate (1000 ml), washed with dilute HCl and brine, dried ($Na_2SO_4$) and evaporated to give an oil. This was dissolved in MeOH (300 ml), and a solution of methanolic HCl (formed by cautious addition of thionyl chloride (20 ml) to MeOH (200 ml)) was added. The solution was stirred at reflux for 2h, evaporated, dissolved in ether, filtered and evaporated again to yield the title compound (97.6 g, quantitative) as an amber oil.

$^1$H NMR (200 MHz, $CDCl_3$) δ (ppm): 7.55 (td, 1H), 7.35 (m, 1H), 7.19 (td, 1H), 7.09 (m, 1 H), 3.62 (s, 6H), 2.1–2.7 (m, 8H).

DESCRIPTION 2

Methyl 5-cyano-5-(2-fluorophenyl)-2-oxocyclohexane-1-carboxylate

Dimethyl 4-cyano4-(2-fluorophenyl)heptanedioate (D1, 35.86 g, 0.12 mol) was stirred under Ar in toluene (500 ml) as sodium hydride (80% in mineral oil, 3.5 g, 0.12 mol) was added. Methanol (10 ml) was added dropwise, and the mixture was then stirred at reflux for 16 h, partitioned between ethyl acetate and dilute HCl, and separated. The organic portion was washed with brine, dried ($Na_2SO_4$) and evaporated to an oil. This was dissolved in dichloromethane (500 ml), filtered, and evaporated to give the title compound (30.66 g, 95%) as a cream solid.

$^1$H NMR (250 MHz, $CDCl_3$) (predominantly enol form) δ (ppm): 12.27 (s, 1H), 7.1–7.6 (m, 4H), 3.80 (s, 3H), 3.09 (d, 1H), 2.85 (m, 2H), 2.2–2.7 (m, 3H).

DESCRIPTION 3

1-(2-Fluorophenyl)-4-oxocyclohexane-1-carboxylic acid

Methyl 5-cyano-5-(2-fluorophenyl)-2-oxocyclohexane-1-carboxylate (D2, 30.66 g, 0.11 mol) was stirred at reflux in c. HCl (500 ml) for 17 h, cooled, diluted with water (500 ml), and extracted with ethyl acetate. This organic portion was washed with potassium carbonate solution, dried (Na$_2$SO$_4$) and evaporated to give 4-cyano-4-(2-fluorophenyl)cyclohexanone (9.58 g, 38%) as a yellow foam. The alkaline wash was re-acidified with c. HCl, and the product isolated by extraction with ethyl acetate, drying (Na$_2$SO$_4$) and evaporation. This gave the title compound (16.36 g, 62%) as a colourless gum.

$^1$H NMR (200 MHz, CDCl) ε (ppm): 7.0–7.4 (m, 4H), 2.55–2.9 (m, 4H), 2.2–2.55 (m, 4H).

DESCRIPTION 4

1'-(2-Fluorophenyl)spiro[[1,3]dioxolane-2,4'-cyclohexane]-1'-carboxylic acid 1-(2-Fluorophenyl)4-oxocyclohexane-1-carboxylic acid (D3, 16.36 g, 69 mmol) was stirred with toluene-4-sulphonic acid hydrate (0.50 g, 3 mmol) and 1,2-ethanediol (35 ml) at reflux in toluene (500 ml), removing the immiscible 1,2-ethanediol/water distillate via a Dean-Stark trap until the distillate was homogenous. The solution was then evaporated, dissolved in ethyl acetate, washed with water and brine, dried (Na$_2$SO$_4$) and evaporated to give the title compound (19.94 g, quantitative) as an amber syrup, contaminated with some unidentified materials (NMR).

$^1$H NMR (250 MHz, CDCl$_3$) δ (ppm): 7.1–7.4 (m, 4H), 3.98 (m, 4H), 2.0–2.8 (m, 8H).

DESCRIPTION 5

4'-(2-Fluorophenyl)-4'-(hydroxymethyl)spiro[[1,3]dioxolane-2,1'-cyclohexane]

1'-(2-Fluorophenyl)spiro[[1,3-dioxolane-2,4'-cyclohexane]-1'-carboxylic acid (D4, 19.90 g, 71 mmol) was stirred in THF (500 ml) under Ar as LiAlH$_4$ (5.4 g, 0.14 mol) was added portionwise. The mixture was stirred at reflux for 3 h, cooled and treated successively with water (5.4 ml), 10% NaOH (5.4 ml) and water (16.2 ml). The solids were filtered off, and washed well with ethyl acetate. The combined organics were evaporated to an oil, and purified by chromatography on silica gel, eluting with 50% ethyl acetate/petroleum ether (b.p. 60–80° C.). This gave the title compound (5.44 g, 28%) as a colourless oil.

$^1$H NMR (250 MHz, CDCl$_3$) δ (ppm): 7.0–7.4 (m, 4H), 3.93 (m, 4H), 3.72 (s, 2H), 2.41 (bd, 2H), 1.5–1.9 (m, 6H).

DESCRIPTION 6

Dispiro[benzofuran-3(2H), 1'-cyclohexane-4',2"-[1,3dioxolane]

Sodium hydride (80% in mineral oil, 1.53 g, 51 mmol) was stirred in dry DMF (30 ml) as 4-(2-fluorophenyl)-4'-(hydroxymethyl)spiro[[1,3]-dioxolane-2,1'-cyclohexane] (D5, 5.44 g 20 mmol) was added in dry DMF (70 ml). The mixture was stirred under Ar at 110° C. for 6 h, cooled, diluted with ethyl acetate (500 ml), washed with water and brine, dried (Na$_2$SO$_4$) and evaporated to give the title compound (4.83 g, 96%) as a straw coloured solid.

$^1$H NMR (250 MHz, CDCl$_3$) δ (ppm): 7.15 (m, 2H), 6.88 (t, 1H), 6.79 (d, 1H), 4.39 (s, 2H), 4.00 (s, 4H), 1.6–2.1 (m, 8H).

DESCRIPTION 7

Spiro[benzofuran-3(2H),1'-cyclohexan-4'-one]

Dispiro[benzofuran-3(2H), 1'-cyclohexane-4',2"-[1,3] dioxolane] (D6, 1.77 g, 7.2 mmol) as stirred at reflux in a mixture of THF (100 ml) and 5M HCl (25 ml) for 2 h, cooled, diluted with ethyl acetate (150 ml), washed with water and brine, dried (Na$_2$SO$_4$) and evaporated to give the title compound (1.41 g, 96%) as a yellow solid.

$^1$H NMR (250 MHz, CDCl$_3$) δ (ppm): 7.15 (m, 2H), 6.93 (t, 1H), 6.86 (d, 1H), 4.57 (s, 2H), 2.5 (m, 4H), 2.2 (m, 4H).

DESCRIPTION 8

5-Nitrospiro[benzofuran-3(2H),1'-cyclohexan-4'-one]

Spiro[benzofuran-3(2H), 1'-cyclohexan4'-one] (D7) (1.74 g, 8.6 mmol) was stirred in acetic anhydride (35 ml) and maintained at <20° C. as copper (II) nitrate hemipentahydrate (2.66 g, 11.4 mmol) was added portionwise over 20 min. The mixture was stirred for 3.5 h, poured cautiously into sodium carbonate solution containing a little ammonia (d 0.88), and extracted with ethyl acetate. The extract was dried (Na$_2$SO$_4$) and evaporated to give the title compound (2.07 g, 97%) as an orange solid, containing ca. 20% of the 7-nitro isomer (NMR). Chromatography on silica gel, eluting with 30–100% ethyl acetate in petroleum ether (b.p. 60–80° C.) afforded the pure 5-nitro isomer.

1H NMR (250 MHz, CDCl$_3$) δ (ppm): 8.17 (dd, 1H), 8.05 (d, 1H), 6.90 (d, 1H), 4.75 (s, 2H), 2.4–2.65 (m, 4H), 2.1–2.3 (m, 4H).

DESCRIPTION 9

5-Aminospiro[benzofuran-3(2H), 140 -cyclohexan-4'-one]

5-Nitrospiro[benzofuran-3(2H), 1'-cyclohexan-4'-one] (D8) (1.01 g, 4.1 mmol) was hydrogenated over 10% Pd/C (0.3 g) in acetic acid (25 ml) for 20 h. Catalyst was filtered off onto kieselguhr, and the filtrate was evaporated, dissolved in dichloromethane, washed with sodium carbonate solution, dried (Na$_2$SO$_4$) and evaporated to give the title compound (0.84 g, 95%) as a brown powder.

$^1$H NMR (250 MHz, CDCl$_3$) δ (ppm): 6.5–6.8 (m, 3H), 4.50 (s, 2H), 3.5 (b, 2H), 2.3–2.7 (m, 4H), 2.0–2.3 (m, 4H)

DESCRIPTION 10

2,3-Dihydro-5-[2'-methyl-4'-(5-methyl-1,2,4-oxadiazol-3-yl)biphenyl-4-carbonylamino]spiro[benzofuran-3,1'-cyclohexan-4'-one]

2'-Methyl-4'-(5-methyl-1,2,4-oxadiazol-3-yl)biphenyl-4-carboxylic acid (EP-0533268-A1) (0.34 g, 1.2 mmol) was stirred at reflux under Ar in thionyl chloride (8 ml) for 30 min, cooled, and evaporated to dryness. The residue was dissolved in dichloromethane (5 ml), and 5-aminospiro[benzofuran-3(2H),1'-cyclohexan-4'-one] (D9) (0.25 g, 1.1 mmol) in dichloromethane (5 ml), and triethylamine (0.32 ml, 2.3 mmol) were added. The mixture was stirred for 30 min, and then left to stand for 16 h before washing with potassium carbonate solution, drying (Na$_2$SO$_4$) and evaporation. Chromatography on silica gel, eluting with 0–2% methanol in dichloromethane, gave the title compound (0.43 g, 75%).as a pinkish foam.

$^1$H NMR (250 MHz, CDCl$_3$) δ (ppm): 7.85–8.05 (m, 5H), 7.3–7.5 (m, 4H), 6.84 (d, 1H), 4.60 (s, 2H), 2.67 (s, 3H), 2.34 (s, 3H), 1.5–2.7 (m, 8H)

DESCRIPTION 11

1,4-Dioxaspiro[4,5]dec-7-ene-8-methanol

Methyl 1,4-dioxaspiro[4,5]dec-7-ene-8-carboxylate [*J. Org. Chem.* 40, 538 (1975)] (1.00 g, 5.0 mmol) was stirred under Ar in dry THF (50 ml) at −78° C. as diisobutylaluminium hydride (1.5M in toluene, 8.4 ml, 12.6 mmol) was added dropwise. The mixture was stirred, warming to ambient temperature, for 2.5 h, and then quenched by successive addition of methanol (9 ml), ethanol (9 ml) and water (9 ml). The gelatinous mixture was diluted with ethyl acetate, and filtered through kieselguhr. The filtrate was washed with brine, dried (Na$_2$SO$_4$) and evaporated to give the title compound (0.79 g, 92%) as a colourless oil.

$^1$H NMR (250 MHz, CDCl$_3$) δ (ppm): 5.62 (m, 1H), 4.04 (s, 2H), 4.00 (s, 4H), 2.31 (m, 4H), 1.80 (t, 2H), 1.8 (b, 1H).

DESCRIPTION 12

1-Acetyl-6-bromo-2,3-dihydro-5-(1,4-dioxaspiro[4,5]dec-7-en-8-yl)methoxy-1H-indole 1-Acetyl-6-bromo-2,3-dihydro-1H-indol-5-ol (*Tetrahedron* 1973, 29, 1115) (1.10 g, 4.3 mmol), 1,4-dioxaspiro[4,5]dec-7-ene-8-methanol (D11, 0.88 g, 5.2 mmol) and triphenylphosphine (1.36 g, 5.2 mmol) were stirred under Ar in dry THF (50 ml) as diethyl azodicarboxylate (0.82 ml, 5.2 mmol) was added dropwise. The mixture was stirred for 1 h, diluted with ethyl acetate (100 ml), washed with brine, dried (Na2SO$_4$) and evaporated to give a dark oil. Chromatography on silica gel, eluting with 0–5% methanol/dichloromethane, gave the title compound (3.17 g) contaminated by substantial amounts of triphenylphosphine and diethyl azodicarboxylate-derived residues (NMR).

$^1$H NMR (200 MHz, CDCl$_3$) δ (ppm): 8.44 (s, 1H), 6.73 (s, 1H), 5.77 (m, 1H), 4.42 (s, 2H), 4.06 (t, 2H), 3.99 (s, 4H), 3.13 (t, 2H), 2.35 (m, 4H), 2.20 (s, 3H), 1.84 (t, 2H).

DESCRIPTION 13

5-Acetyl-2,3,6,7-tetrahydrodispiro[furo[2,3-f]indole-3,1'-cyclohexane4',2''-[1,3-dioxolane]

1-Acetyl-6-bromo-2,3-dihydro-5-(1,4-dioxaspiro[4,5]dec-7-en-8-yl)methoxy-1H-indole (D12, 3.17 g from 4.3 mmol D11) and α,α'-azoisobutyronitrile (0.05 g) were stirred at reflux in benzene (160 ml) under Ar as tributyltin hydride (1.75 ml, 6.5 mmol) was added dropwise in benzene (40 ml) over 20 min. The mixture was then stirred at reflux for 3 h, cooled, evaporated, and chromatographed on silica gel, eluting with 0–3% methanol/dichloromethane. This gave the title compound (2.62 g), again contaminated by substantial amounts of triphenylphosphine and diethyl azodicarboxylate-derived residues (NMR).

$^1$H NMR (250 MHz, CDCl$_3$) δ (ppm): 8.09 (s, 1H), 6.62 (s, 1H), 4.40 (s, 2H), 4.05 (t, 2H), 3.98 (s, 4H), 3.13 (t, 2H), 2.20 (s, 3H), 2.1 (m, 2H), 1.5–1.9 (m, 6H).

DESCRIPTION 14

2,3,6,7-Tetrahydrospiro[furo[2,3-f]indole-3,1'-cyclohexan-4'-one]

5-Acetyl-2,3,6,7-tetrahydrodispiro [furo[2,3-f]indole-3,1'-cyclohexane-4'-,2''-[1,3]-dioxolane] (D13, 2.41 g) was stirred at reflux in a mixture of 5M hydrochloric acid (100 ml) and ethanol (40 ml) for 2 h, cooled, evaporated to remove ethanol, basified (K$_2$CO$_3$), and extracted with dichloromethane. The extract was dried (Na$_2$SO$_4$) and evaporated to give a brown oil. This was purified by chromatography on silica gel, eluting with 0–80% ethyl acetate/dichloromethane, giving the title compound as a light yellow solid (1.30 g), still contaminated by substantial amounts of triphenylphosphine- and diethylazodicarboxylate-derived residues (NMR).

$^1$H NMR (250 MHz, CDCl$_3$) δ (ppm): 6.67 (s, 1H), 6.48 (s, 1H), 4.50 (s, 2H), 3.56 (t, 2H), 2.99 (t, 2H), 2.47 (m, 4H), 2.10 (m, 4H).

DESCRIPTION 15

4'-Dimethylamino-2,3,6,7-tetrahydrosprio[furo[2,3-f]indole-3,1'-cyclohexane]

2,3,6,7-Tetrahydrospiro[furo[2,3-f]indole-3,1'-cyclohexan-4'-one] (D14, 1.30 g) and dimethylamine (5.6M in ethanol, 2 ml, 11 mmol) were stirred in 1,2-dichloroethane (100 ml), and sodium triacetoxyborohydride (2.27 g, 10.7 mmol) was added. The mixture was stirred for 18 h, diluted with ethyl acetate, and extracted with dilute hydrochloric acid. The extract was basified with saturated K$_2$CO$_3$ solution, and extracted with dichloromethane. This organic extract was dried (Na$_2$SO$_4$) and evaporated to give the title compound (0.37 g, 35% over Descriptions 12–15) as a brown oil. NMR showed ca. 1:1 mixture of isomers.

$^1$H NMR (200 MHz, CDCl$_3$) δ (ppm): 6.77 (s, 0.5H), 6.62 (s, 1H), 6.41 (s, 0.5H), 4.31 (s, 1H), 4.18 (s, 1H), 3.53 (t, 2H), 2.96 (t, 2H), 2.32 (s, 3H), 2.31 (s, 3H), 1.2–2.2 (m, 9H).

EXAMPLE 1

2,3-Dihydro-4'-dimethylamino-5-[2'-methyl-4'-(5-methyl-1,2,4-oxadiazol-3-yl)biphenyl-4-carbonylamino]spirolbenzofuran-3,1'-cyclohexane], isomers A and B 2,3-Dihydro-5-[2'-methyl-4'-(5-methyl-1,2,4-oxadiazol-3-yl)biphenyl-4-carbonylamino]spiro[benzofuran-3,1'-cyclohexan-4'-one] (D10) (0.43 g, 0.87 mmol), dimethylamine hydrochloride (0.21 g, 2.6 mmol) and sodium cyanoborohydride (0.09 g, 1.4 mmol) were stirred in methanol (20 ml)/dichloromethane (10 ml) for 6 days. The mixture was then diluted with dichloromethane, washed with potassium carbonate solution, dried (Na$_2$SO$_4$) and evaporated. Chromatography on silica gel, eluting with 0–30% methanol/dichloromethane, afforded the two isomers of the title compound:

Isomer A (less polar; 0.042 g (9%))

Isomer B (more polar; 0.026 g (6%))

Both isomers were converted to their oxalate salt, which were white powders.

Isomer A (axial NMe$_2$, substituent), oxalate salt: $^1$H NMR (400 MHz, d$^6$DMSO) δ (ppm): 10.02 (s, 1H), 8.05 (d, 2H), 8.01 (d, 1H), 7.96 (s, 1H), 7.90 (d, 1H), 7.50 (m, 3H), 7.41 (d, 1H), 6.77 (d, 1H), 4.23 (s, 2H), 3.17 (m, 1H), 2.79 (s, 6H), 2.67 (s, 3H), 2.34 (s, 3H), 1.97 (m, 6H), 1.66 (m, 2H).

Isomer B (equatorial NMe$_2$ Substituent), oxalate salt: $^1$H NMR (400 MHz, d$^6$DMSO) δ (ppm): 10.20 (s, 1H), 8.04 (d, 2H), 7.98 (s, 1H), 7.91 (d, 1H), 7.70 (d, 1H), 7.56 (d, 1H), 7.44 (d, 1H), 7.41 (dd, 1H), 6.78 (d, 1H), 4.41 (s, 2H), 3.28 (m, 1H), 2.73 (s, 6H), 2.69 (s, 3H), 2.36 (s, 3H), 2.01 (m, 2H), 1.86 (m, 2H), 1.74 (m, 2H), 1.54 (m, 2H).

EXAMPLE 2

4'-Dimethylamino-5-[2'-methyl4'-(5-methyl-1,2,4-oxadiazol-3-yl)biphenyl-4-carbonyl]-2,3,6,7-tetrahydrospiro[furo[2,3-f]indole-3,1'-cyclohexane]

This was prepared from 4'-dimethylamino-2,3,6,7-tetrahydrospiro[furo[2,3-f]indole-3,1-'cyclohexane] (D15), following the procedure of Description 10. Chromatography required elution with 0–20% methanol/dichloromethane. This gave the title compound (71%) as a colourless gum, which was converted to its hydrochloride salt. NMR showed a ca. 1:1 mixture of isomers.

$^1$H NMR (HCl salt) (200 MHz, d$^6$DMSO) δ (ppm): 10.67 (b, 0.5H), 10.48 (b, 0.5H), 8.35 (b, 0.5H), 7.85–8.0 (m, 2.5H), 7.66 (m, 2H), 7.4–7.6 (m, 3H), 6.76 (s, 0.5H), 6.73 (s, 0.5H), 4.40 (s, 1H), 4.26 (s, 1H), 4.08 (m, 2H), 3.03 (m, 2H), 2.81 (s, 3H), 2.69 (s, 6H), 2.38 (s, 3H), 1.5–2.2 (m, 8H). 1H signal not discernable in spectrum.

I claim:

1. A compound of formula (I) or a salt or N-oxide thereof:

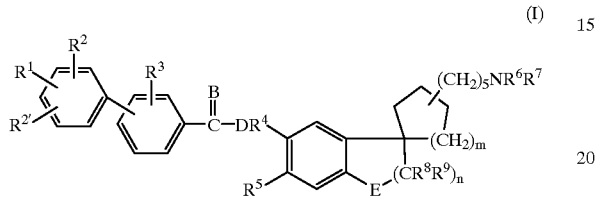

(I)

in which

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^{10}$, SOR$^{10}$, SO$_2$R$^{10}$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 and R$^{13}$ is hydrogen, C$_{1-6}$alkyl or optionally substituted aryl; or R$^1$ is a group —X—R where X is a bond, O, S, CH$_2$, C=O, NHCO, NAlkylCO, NH or NAlkyl where Alkyl is C$_{1-6}$alkyl and R is an optionally substituted bicyclic heterocyclic ring or monocyclic 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ areas defined for R$^1$;

B is oxygen or sulphur;

D is nitrogen, carbon or a CH group;

R$^4$ is hydrogen or C$_{1-6}$alkyl;

R$^5$ is hydrogen or C$_{1-6}$alkyl or R$^4$ and R$^5$ together form a group —A— where A is (CR$^{13}$R$^{14}$)$_q$ where q is 2, 3 or 4 and R$^{13}$and R$^{14}$ are independently hydrogen or C$_{1-6}$alkyl or A is (CR$^{13}$R$^{14}$)$_r$—D where r is 0, 1, 2 or 3 and D is oxygen, sulphur or CR$^{13}$=CR$^{14}$;

R$^6$ and R$^7$ are independently hydrogen, C$_{1-6}$alkyl or R$^6$ and R$^7$ are joined to form an optionally substituted 5- to 7-membered heterocyclic ring optionally containing a further heteroatom selected from oxygen, nitrogen or sulphur;

R$^8$ and R$^9$ are independently hydrogen or C$_{1-6}$alkyl;

E is oxygen, CR$^{15}$R$^{16}$ or NR$^{17}$ where R$^{15}$, R$^{16}$ and R$^{17}$ are independently hydrogen or C$_{1-6}$alkyl or E is a group S(O)$_b$ where b is 1, 2 or 3;

m is 1, 2 or 3;

n is 1, 2 or 3; and s is 0, 1, 2, 3 or 4.

2. A compound according to claim 1 in which R$^1$ is a group —XR where X is a bond and R is optionally substituted oxadiazole.

3. A compound according to claim 1 in which R$^2$ is C$_{1-6}$alkyl.

4. A compound according to claim 1 in which m is 2.

5. A compound according to claim 1 in which n is 1.

6. A compound according to claim 1 which is:

2,3-Dihydro-4'-dimethylamino-5-[2'-methyl-4'-(5-methyl-1,2,4-oxadiazol-3-yl)biphenyl-4-carbonylamino]spiro[benzofuran-3,1'-cyclohexane],
4'-Dimethylamino-5-[2'-methyl-4'-(5-methyl-1,2,4-oxadiazol-3-yl)biphenyl-4-carbonyl]-2,3,6,7-tetrahydrospiro[furo[2,3-f]indole-3,1'-cyclohexane], or pharmaceutically acceptable salts or N-oxides thereof.

7. A process for the preparation of a compound of formula (I) which comprises:

(a) for compounds where D is nitrogen and B is oxygen reaction of a compound of formula (II):

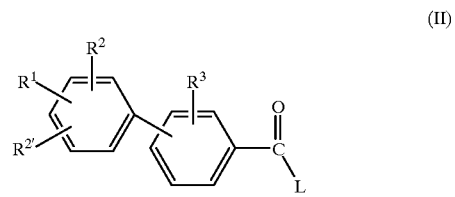

(II)

in which R$^1$, R$^2$, R$^{2'}$ and R$^3$ are as defined in formula (I) and L is a leaving group, with a compound of formula (III):

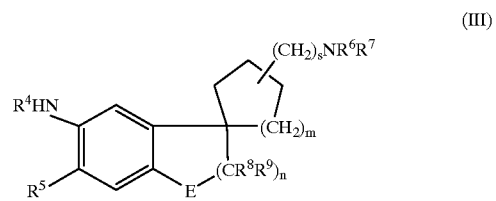

(III)

wherein R$^4$, R$^5$, R$^6$, R$^7$, R$^8$, R$^9$, E, m, n and s are as defined in formula (I) and optionally thereafter in any order:

converting a compound of formula (I) into another compound of formula (I)

forming a pharmaceutically acceptable salt or N-oxide thereof.

8. A pharmaceutical composition which comprises a compound according to claim 1 in association with a pharmaceutically acceptable carrier or excipient.

* * * * *